United States Patent [19]

Schilling

[11] 4,242,276
[45] Dec. 30, 1980

[54] PROCESS FOR THE MANUFACTURE OF β-ISOBUTYRYLAMINOCROTONIC ACID AMIDE

[75] Inventor: Bernd Schilling, Munich, Fed. Rep. of Germany

[73] Assignee: Consortium für Elektrochemische Industrie GmbH, Munich, Fed. Rep. of Germany

[21] Appl. No.: 99,778

[22] Filed: Dec. 3, 1979

[30] Foreign Application Priority Data

Dec. 14, 1978 [DE] Fed. Rep. of Germany ....... 2853887

[51] Int. Cl.$^3$ .............................................. C07C 97/16
[52] U.S. Cl. ..................................................... 564/159
[58] Field of Search .......... 260/561 A, 561 N, 561 K, 260/561 R

[56] References Cited

U.S. PATENT DOCUMENTS

| | | | |
|---|---|---|---|
| 3,367,947 | 2/1968 | Cornforth | 260/561 K |
| 3,458,573 | 7/1969 | Tieman | 260/561 K |
| 3,459,801 | 8/1969 | Beriger | 260/561 K |
| 3,483,252 | 12/1969 | Beriger | 260/561 K |
| 3,703,518 | 11/1972 | Inol et al. | 260/561 A |
| 4,129,596 | 12/1978 | Kunstle et al. | 260/561 K |

OTHER PUBLICATIONS

Kato et al., Tetrahedron 23 (1967) p. 2965–2971.

*Primary Examiner*—Arthur P. Demers
*Attorney, Agent, or Firm*—Allison C. Collard; Thomas M. Galgano

[57] ABSTRACT

A process for the manufacture of β-isobutyrylaminocrotonic acid amide by reacting β-aminocrotonic acid amide with dimethylketene in the liquid or gaseous state without the application of external heat at temperatures in the range of from room temperature to 70° C. The dispersion medium used is an organic solvent having a boiling point above 40° C. that may contain up to 0.1 mole of water and 0.2 to 2 moles of a carboxylic acid having 1 to 4 carbon atoms per mole of β-aminocrotonic acid amide. If the dimethylketene is added undiluted the reaction is carried out in the absence of oxygen and in the presence of a protective gas atmosphere. The β-isobutyrylaminocrotonic acid amide is obtained in the form of two stereoisomers (Z- and E-forms), which differ as regards their melting point and their solubility in organic solvents. On heating to 40° C., the E-form is converted into the Z-form.

8 Claims, No Drawings

PROCESS FOR THE MANUFACTURE OF β-ISOBUTYRYLAMINOCROTONIC ACID AMIDE

The present invention relates to a process for the manufacture of β-isobutyrylaminocrotonic acid amide.

It is known that β-aminocrotonic acid amide, readily available from diketene and ammonia, can be N-acylated by the action of acide anhydrides or acid chlorides as acylating agents to form the corresponding β-acylaminocrotonic acid amides. For example, by the action of isobutyric acid anhydride by refluxing in chloroform, β-isobutyrylaminocrotonic acid amide is obtained in a yield of 62% (cf. JP-AS 68 03.363, ref. C.A. vol. 69 (1968), page 6263).

This process is uneconomical in practice, however, both with respect to the isobutyric acid anhydride, which is difficult to obtain, and with respect to the moderate yields which are coupled with high expenditure owing to the fact that several purifying steps are necessary in order to separate, from the desired product, unreacted starting material and the isobutyric acide formed as by-product.

A process for the manufacture of β-isobutyrylaminocrotonic acid amide has now been found, according to the present invention, that renders possible the reaction of β-aminocrotonic acid amide with an isobutyryl compound as acylating agent in approximately stoichiometric amounts, in the presence of a solvent, under mild conditions, resulting in good yields, without expensive purifying steps for separating by-products or unreacted starting material being necessary.

The process according to the invention is characterized in that dimethylketene is used as the acylating agent and the reaction is carried out in the temperature range from room temperature to 70° C. without external application of heat.

The process according to the invention may be illustrated by the following equation:

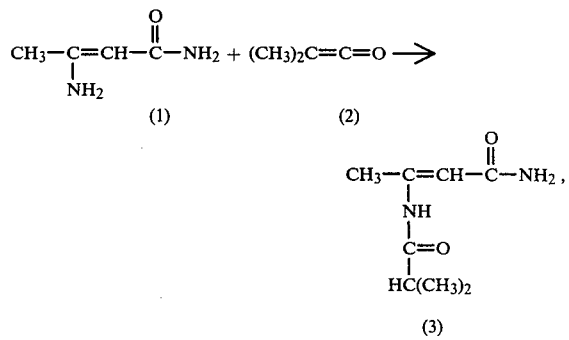

in which the desired compound (3) is obtained in yields of up to 90% of the theoretical yield. It is clear from this that the action of dimethylketene results practically exclusively in N-acylation. This result must be considered surprising especially in view of the investigations by T. Kato et al. in "Heterocycles", vol. 3, No. 5, 1975, pages 419 and 421, which demonstrate that the action of ketene on β-aminocrotonic acid amide proceeds practically exclusively by way of the formation of C-acylation products.

In the process according to the invention, the desired compound (3) is produced in the form of 2 stereoisomers which are probably of the following configurations:

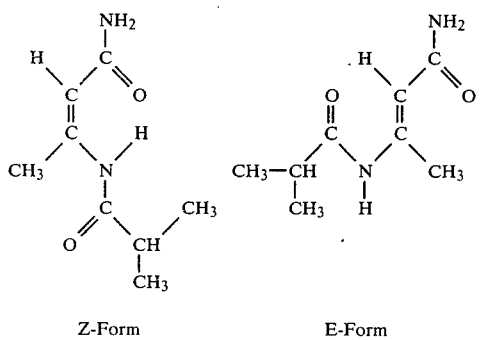

Z-Form             E-Form

The stereoisomeric compound (3) referred to hereinafter as the Z-form has a melting point of 148° C. and is readily soluble in chloroform and acetone. It is the main product in the process according to the invention. The stereoisomeric compound (3) referred to hereinafter as the E-form has a melting point of 210° C. and is sparingly soluble in chloroform and acetone. In the process according to the invention, it is produced in quantities of 6 to 18% depending on the selected reaction conditions, which will be explained in detail hereinafter. Owing to the differences of solubility in the mentioned solvents, the two stereoisomers can easily be separated from one another. However, this is not absolutely necessary because the E-form is converted into the Z-form on heating to 40° C.

β-isobutyrylaminocrotonic acid amide is a useful starting material for the manufacture of 2-isopropyl-6-methyl-4-hydroxypyrimidine, which is required as an intermediate for the manufacture of 0,0-diethyl-0-(2-isopropyl-6-methyl-4-pyrimidyl) thionophosphate which is marketed as a quick-acting contact insecticide under the trademark "Diazinon".

In the manufacture of the mentioned pyrimidine derivative, the β-isobutyrylaminocrotonic acid amide is heated under alkaline conditions and the pyrimidine ring is formed from the stereoisomeric Z-form by ring closure. Since, in any case, temperatures of above 40° C. are necessary for this reaction, the two stereoisomeric forms of β-isobutyrylaminocrotonic acid amide can equally be used for this process; that is to say, it is not necessary to separate the mixture of the two stereoisomers obtained according to the process of the invention.

When carrying out the process according to the invention, the β-aminocrotonic acid amide is advantageously dispersed in an organic solvent having a boiling point above 40° C. Examples of such dispersion media are halogenated aliphatic hydrocarbons, such as chloroform and tetrachloroethylene, aromatic hydrocarbons, such as toluene and xylene, substituted aromatic hydrocarbons, such as chlorobenzene and nitrobenzene, carboxylic acid esters, such as ethyl acetate and butyl acetate, carboxylic acid anhydrides, such as isobutyric acid anhydride, nitriles, such as acetonitrile and isobutyronitrile, ethers, such as tetrahydrofuran, dioxan and diethylene glycol ether, and also ketones such as acetone, methyl ethyl ketone and cyclohexanone.

It is not absolutely necessary for the dispersion medium used to be completely anhydrous. Small quantities of water can be tolerated in the solvent, that is to say up to approximately 1 mole of water per mole of β-aminocrotonic acid amide. Larger quantities of water must be avoided as they impair the yield. It has been shown, however, that the presence of water in quantities of up to approximately 0.1 mole per mole of β-aminocrotonic acid amide produces an increase in yield.

It is furthermore advantageous to buffer the dispersion medium by adding organic acids, so as to prevent the strongly basic β-aminocrotonic acid amide acting as a catalyst to the self-reaction of the dimethylketene. Suitable organic acids are carboxylic acids preferably having 1 to 4 carbon atoms, such as formic, acetic, propionic or butyric acid, isobutyric acid having proved particularly suitable. The quantities of organic carboxylic acids added may vary within the range of from 0.2 to 2 moles of acid per mole of β-aminocrotonic acid amide.

The addition of an organic acid is advantageous especially when using non-polar solvents, such as toluene or xylene, in which the β-aminocrotonic acid amide does not completely dissolve because, as a result, the solubility of the starting material is improved and the yields of the desired product are increased. The addition of the acid furthermore promotes the formation of the stereoisomeric E-form.

In the process according to the invention, the reactants, i.e., β-aminocrotonic acid amide and dimethylketene, are used in approximately stoichiometric amounts. A slight excess of dimethylketene in the range of approximately 0.2 to 0.4 mole is, however, advantageous for obtaining high yields of the desired end product. A larger excess should be avoided, however, since this involves the risk of the desired end product being contaminated by polymeric products from the dimethylketene which has a tendency towards self-reaction. Although the use of less than the stoichiometric amount of diemthylketene substantially suppresses such a reaction, it results, especially in a discontinuous method of operation, in a reduction in yield.

When carrying out the process according to the invention, the dimethylketene is introduced in gaseous or liquid state into the β-aminocrotonic acid amide dispersed in the solvent. The reaction, which begins at room temperature, is exothermic, so that the external application of heat is not necessary. Temperatures of up to approximately 70° C. should not be exceeded, however, and this can be achieved by controlling the speed of addition of the dimethylketene and/or by cooling from the outside. The best results are obtained at operating temperatures in the range from 40° to 60° C.

Liquid dimethylketene (boiling point 34° C.) can be introduced undiluted or dissolved in an inert organic solvent. When it is added undiluted, the reaction is advantageously carried out in the absence of oxygen, that is to say in the presence of a protective gas atmosphere, such as nitrogen. Examples of inert organic solvents are solvents free of carbonyl groups, which may also be used for dispersing the β-aminocrotonic acid amide, and ethers with low boiling points, such as diethyl ether. The reaction is usually carried out under normal pressure, thorough mixing of the reactants being ensured by mechanical agitation.

If gaseous dimethylketene is used, it is advantageously introduced undiluted into the reaction medium under reduced pressure and in the presence of a protective gas atmosphere, a reduced pressure in the range of 50 to 300 mbar having proved especially suitable. The introduction of the gas can, however, be carried out at normal pressure or slightly elevated pressure, such as is produced by the presence of a flowing protective gas atmosphere. Introduction in the gaseous form already provides for thorough mixing of the reactants, but this can be assisted, if desired, by mechanical agitation.

If these conditions are observed, the reaction is generally complete after approximately 15 minutes to approximately 4 hours if operating discontinuously, and this can be observed visually by the disappearance of the yellow color of the dimethylketene.

The process can, however, also be carried out continuously, in which case contact times of approximately 15 minutes should not be exceeded.

When the reaction is complete, the isomeric mixture formed is filtered off or is freed of volatile constituents under reduced pressure, and optionally purified by recrystallization.

The process according to the invention is more fully explained in the following Examples, which are given by way of illustration and not of limitation.

EXAMPLE 1

A solution of 10 g. (0.1 mole) of a β-aminocrotonic acide amide in 100 ml of diethylene glycol dimethyl ether was introduced into a reaction vessel fitted with a reflux condenser, a dropping funnel and stirring means. Then, while stirring, 40 ml of a solution of dimethylketene (0.12 mole) in diethyl ether were added dropwise over the course of 10 minutes, the temperature increasing to approximately 50° C. When the addition was complete, the precipitated E-β-isobutyrylaminocrotonic acid amide was filtered off (1.1 g=6.5% yield) and the remaining solution was freed of volatile constituents under reduced pressure. The residue was washed with water and extracted several times with chloroform. The solvent was then removed from the organic phase and the residue was recrystallized from toluene. 13.4 g (=78.8% yield) of colorless crystallized Z-β-isobutyrylaminocrotonic acid amide were obtained.

The total yield of β-isobutyrylaminocrotonic acid amide was 85.3% of the thereoretical yield, calculated on the β-aminocrotonic acid amide used.

ANALYTICAL DATA

E-β-isobutyrylaminocrotonic acid amide
  m.p. 210° C.
  NMR-spectrum (DMSO, -$d_6$-TMS as internal standard) 1.09, d, J=6.5 Hz, 6H; 2.28, S, 3H; 2.6; Sept., J=6.5 Hz, 1H; 6.72, S, 1H; 6.81 d, J=50 Hz, 2H; 9.18, S, 1H;

Z β-isobutyrlaminocrotonic acid amide:
  148° C.
  NMR-spectrum (DMSO, -$d_6$-TMS as internal standard) 1.14, d, J=6.5 Hz, 6H; 2.26, S, 3H; 2.38 Sept., J=6.5 Hz, 1H; 4.94, S, 1H; 7.10, d, J=42 Hz, 2H; 12.31, S, 1H.

EXAMPLE 2

The process described in Example 1 was repeated except that the βaminocrotonic acid amide was dissolved in 100 ml of acetone.

1.7 g=10% yield of E-β-isobutyrylaminocrotinic acid amide and 13.7 g=80.6% yield of Z-β-isobutyrylaminocrotonic acid amide were obtained. The total yield of β-isobutyrylaminocrotonic acid amide was 90.6% of the theoretical yield.

EXAMPLE 3

The process described in Example 1 was repeated with the following variations:

6 g(0.06 mole) of β-aminocrotonic acid amide were dissolved in 60 ml of nitrobenzene. Then, while stirring, 5.88 g (0.084 mole) of dimethylketene, diluted with 10 ml of nitrobenzene, were added dropwise over the course of 10 minutes. When the addition was complete, the reaction mixture was left to stand at room temperature for 24 hours. The resulting crystalline solid was then filtered off and washed with petroleum ether having a low boiling point. 8 g (=78.4% yield) of Z/E-isomeric mixture were obtained. A further 1.15 g (=11.3% yield) of Z-isomer were obtained from the mother liquor by precipitation with petroleum ether and recrystallization from toluene.

The total yield of β-isobutyrylaminocrotonic acid amide was 89.7% of the theoretical yield.

EXAMPLE 4

The process described in Example 1 was repeated with the following variations:

10 g (0.1 mole) of β-aminocrotonic acid amide were dissolved in 100 ml of chloroform and 1.85 ml (0.02 mole) of isobutyric acid were added. Then, while stirring, 40 ml of a solution of dimethylketene (0.14 mole) in diethyl ether were added dropwise in the course of 10 minutes.

3.2 g (=18.8%) of E-β-aminocrotonic acid amide and 11.3 g (=66.5%) of Z-βisobutyrylaminocrotonic acid amide were obtained.

The total yield of 85.3 % of the theoretical yield.

EXAMPLE 5

The process described in Example 1 was repeated with the following variations:

10 g (0.1 mole) of β-aminocrotonic acid amide were suspended in 100 ml of toluene. Then, while stirring, 9.1 g (0.13 mole) of dimethylketene, diluted with 10 ml of toluene, were added dropwise over the course of 10 minutes. When the addition was complete, the precipitated E/Z-isomeric mixture was filtered off and washed with petroleum ether. The total yield was 14.2 g=83.5% of the theoretical yield.

EXAMPLE 6

A reaction vessel fitted with a reflux condenser, a dropping funnel and a gas inlet pipe was charged with a solution of 4 g (0.04 mole) of β-aminocrotonic acid amide in 40 of isobutyric acid anhydride and 3.7 ml (0.04 mole) of isobutyric acid. Then the reaction vessel was rinsed with nitrogen and, over the course of 5 minutes, 5 ml (0.046 mole) of dimehtylketene were added dropwise under nitrogen, the temperature increasing to approximately 70° C. When the addition was complete and the reaction mixture had cooled, the precipitated Z/E-isomeric mixture was filtered off and washed with petroleum ether.

Yield: 2.8 g=41.2%.

A further 3.2 g=47.1% of Z-isomer were obtained from the mother liquor by precipation with petroleum ether.

The total yield was 88.3% of the theoretical yield.

EXAMPLE 7

The process described in Example 6 was repeated with the following variation:

4 g (0.04 mole) of β-aminocrotonic acid amide were dissolved in 40 ml. of isobutyronitrile and 3.7 ml (0.04 mole) of isobutyric acid.

2.4 g=35.3% of Z/E-isomeric mixture were filtered off and 3.6 g=52.9% of Z-isomer were obtained from the mother liquor.

The total yield of β-isobutyrylaminocrotonic acid amide was 88.2 % of the theoretical yield.

EXAMPLE 8

A solution of 30 g (0.3 mole) of β-aminocrotonic acid amide in 300 ml of diethylene glycol dimethyl ether was introduced under nitrogen into an evacuable reaction vessel fitted with a gas inlet. Then, under a reduced pressure of 100 mbar, 25 g (0.35 mole) of gaseous dimethylketene were introduced over the course of 4 hours, the temperature increasing to approximately 35° C. Air was then fed into the reaction vessel and 9 g=17.6% of E-β-isobutyrylaminocrotonic acid amide were filtered off from the reaction mixture. After distilling off the solvent and recrystallizing the residue from toluene, 34.5 g=67.6% of Z-isomer were obtained from the solution. The total yield of β-isobutyrylaminocrotonic acid amide was 85.2% of the theoretical yield.

EXAMPLE 9

The process described in Example 8 was repeated except that the β-aminocrotonic acid amide was dispersed in 300 ml of isobutyric acid anhydride.

31.2 g=61.2% of Z/E-isomer were filtered off from the solution. By working up the mother liquor, 13.3 g=26.1% of Z-isomer were isolated.

The total yield of β-isobutyrylaminocrotonic acid amide was 87.3% of the theoretical yield.

EXAMPLE 10

A suspension of 10 g (0.1 mole) of β-aminocrotonic acid amide in 100 ml of xylene was introduced into a pressure vessel fitted with a flow-through gas pipe. Then, over the course of 2 hours, 9 g (0.128 mole) of gaseous diketene was passed through in a flowing nitrogen atmosphere. Air was subsequently introduced into the reaction vessel and 13.8 g of Z/E-isomeric mixture were filtered off from the solution.

The total yield of β-isobutyrylaminocrotonic acid amide was 81.2% of the theoretical yield.

EXAMPLE 11

In accordance with the process described in Example 1, in each case 4 g (0.04 mole) of β-aminocrotonic acid amide, dissolved in 40 ml of diethylene glycol dimethyl ether and 3.52 g (0.04 mole) of isobutyric acid, were reacted with 5 ml (0.046 mole) of dimethylketene in the presence of different quantities of water. After working up in accordance with Example 1, the following yields were obtained:

(a) without the addition of water: 4.6 g=67.5% of Z-isomer; 0.9 g=13.2% of E-isomer; total yield: 80.7%.

(b) with 0.072 g of $H_2O$ (0.004 mole) 4.7 g=69.1% of Z-isomer; 1.1 g=16.2% of E-isomer; total yield: 85.3%.

(c) with 0.36 g of $H_2O$ (0.02 mole) 4.4 g=64.7% of Z-isomer; 1.0 g=14.7% of E-isomer; total yield: 79.4%.

(d) with 0.72 g of $H_2O$ (0.04 mole) 4.3 g=63.2% of Z-isomer; 0.9 g=13.2% of E-isomer; total yield: 76.4%.

(e) with 1.44 g of H₂O (0.08 mole) 3.8 g=55.8% of Z-isomer; 0.3 g=4.4% of E-isomer; total yield: 60.2%.

What is claimed is:

1. A process for the manufacture of β-isobutyrylaminocrotonic acid amide by reacting β-aminocrotonic acid amide with an isobutyryl compound as acylating agent in approximately stoichiometric amounts, in the presence of a solvent and with heating, characterized in that dimethylketene is used as the acylating agent and the reaction is carried out in the range of from room temperature to 70° C. with applicaton of external heat.

2. The process according to claim 1, wherein the dimethylketene is introduced into the β-aminocrotonic acid amide dispersed in an organic solvent that has a boiling point above 40° C.

3. The process according to claim 2, wherein the dispersion medium used contains up to 0.1 mole of water per mole of β-aminocrotonic acid amide.

4. The process according to claim 2, wherein the dispersion medium used contains 0.2 to 2 moles of carboxylic acid having 1 to 4 carbon atoms.

5. The process according to claim 1, wherein the dimethylketene is used in a molar excess of from 0.2 to 0.4 mole.

6. The process according to claim 1, wherein liquid dimethylketene is introduced, undiluted, in the absence of oxygen and in the presence of a protective gas atmosphere at normal pressure.

7. The process according to claim 1, wherein gaseous dimethylketene is introduced, undiluted, under a reduced pressure in the range of 50 to 300 mbar, in the presence of a protective gas atmosphere.

8. The process according to claim 1, wherein gaseous dimethylketene is introduced in the presence of a flowing protective gas atmosphere.

* * * * *

UNITED STATES PATENT OFFICE
CERTIFICATE OF CORRECTION

Patent No. 4,242,276  Dated Dec. 30, 1980

Inventor(s) Bernd Schilling

It is certified that error appears in the above-identified patent and that said Letters Patent are hereby corrected as shown below:

Column 4, line 39, change "thereoretical" to --theoretical--; line 49, change "β-isobutyrlaminocrotonic" to --β-isobutyrylaminocrotonic--; line 50, "148°C" change to --m.p. 148°C; line 60, change "E-β-isobutyrylaminocrotinic" to --E-β-isobutyrylaminocrotonic. Column 5, line 48, change "40 of" to --40 ml of--; line 51, change "dimehtylketene" to --dimethylketene--. Column 6, line 22, change "the" to --The-- and start a new paragraph. Claim 4, line 2, after "of" insert --a--.

Signed and Sealed this

Second Day of February 1982

[SEAL]

Attest:

Attesting Officer

GERALD J. MOSSINGHOFF

Commissioner of Patents and Trademarks